(12) United States Patent
Goto

(10) Patent No.: US 8,172,777 B2
(45) Date of Patent: May 8, 2012

(54) SENSOR-BASED HEALTH MONITORING SYSTEM

(75) Inventor: Hiroshi Goto, Ibaraki (JP)

(73) Assignee: Empire Technology Development LLC, Wilmington, DE (US)

( * ) Notice: Subject to any disclaimer, the term of this patent is extended or adjusted under 35 U.S.C. 154(b) by 157 days.

(21) Appl. No.: 12/559,228

(22) Filed: Sep. 14, 2009

(65) Prior Publication Data

US 2011/0066081 A1 Mar. 17, 2011

(51) Int. Cl.
- *A61B 23/00* (2006.01)
- *A61B 5/08* (2006.01)
- *A61B 5/103* (2006.01)
- *A61B 5/117* (2006.01)

(52) U.S. Cl. ............... 600/595; 340/573.1; 600/534; 600/587

(58) Field of Classification Search .......... 600/587, 600/595, 534; 340/573.1
See application file for complete search history.

(56) References Cited

U.S. PATENT DOCUMENTS

| | | | | |
|---|---|---|---|---|
| 4,409,983 A * | 10/1983 | Albert | | 600/503 |
| 4,576,179 A * | 3/1986 | Manus et al. | | 600/484 |
| 4,696,307 A * | 9/1987 | Montgieux | | 600/534 |
| 5,086,785 A * | 2/1992 | Gentile et al. | | 600/595 |
| 5,295,490 A * | 3/1994 | Dodakian | | 600/534 |
| 5,640,971 A * | 6/1997 | Martin, Jr. | | 600/594 |
| 6,062,216 A * | 5/2000 | Corn | | 128/204.23 |
| 6,095,984 A * | 8/2000 | Amano et al. | | 600/500 |
| 6,816,266 B2 * | 11/2004 | Varshneya et al. | | 356/477 |
| 6,917,293 B2 * | 7/2005 | Beggs | | 340/573.1 |
| 7,378,975 B1 * | 5/2008 | Smith et al. | | 340/573.1 |
| 7,420,472 B2 * | 9/2008 | Tran | | 340/573.1 |
| 7,548,168 B2 * | 6/2009 | Ishikawa et al. | | 340/573.1 |
| 7,652,581 B2 * | 1/2010 | Gentry et al. | | 340/573.1 |
| 7,666,151 B2 * | 2/2010 | Sullivan et al. | | 600/587 |
| 7,670,295 B2 * | 3/2010 | Sackner et al. | | 600/483 |
| 7,775,983 B2 * | 8/2010 | Zhang et al. | | 600/483 |
| 7,956,603 B2 * | 6/2011 | Cochran | | 324/207.17 |
| 2003/0095263 A1 * | 5/2003 | Varshneya et al. | | 356/477 |
| 2003/0135127 A1 * | 7/2003 | Sackner et al. | | 600/536 |
| 2003/0216670 A1 * | 11/2003 | Beggs | | 600/595 |
| 2004/0046668 A1 * | 3/2004 | Smith et al. | | 340/573.7 |
| 2004/0116837 A1 * | 6/2004 | Yamaguchi et al. | | 600/595 |
| 2006/0100530 A1 * | 5/2006 | Kliot et al. | | 600/483 |
| 2006/0267779 A1 * | 11/2006 | Ishikawa et al. | | 340/573.1 |
| 2007/0008156 A1 * | 1/2007 | Ueda et al. | | 340/575 |
| 2007/0273504 A1 * | 11/2007 | Tran | | 340/539.12 |

(Continued)

FOREIGN PATENT DOCUMENTS

JP H11-70086 A 3/1999

(Continued)

OTHER PUBLICATIONS

Measurement Specialities, Measurement Specialties Website information, Piezoelectric film sensors used as activity monitors in pacemakers and in monitoring breathing rate, accessed on Sep. 9, 2009, available at http://www.meas-spec.com/downloads/Medical_Instruments.pdf, Hampton, VA, U.S.A.

(Continued)

*Primary Examiner* — Sean Dougherty

(57) ABSTRACT

Implementations for sensor-based health monitoring systems are generally disclosed.

15 Claims, 6 Drawing Sheets

U.S. PATENT DOCUMENTS

| | | | |
|---|---|---|---|
| 2008/0004904 A1* | 1/2008 | Tran | 705/2 |
| 2008/0275349 A1* | 11/2008 | Halperin et al. | 600/484 |
| 2009/0131759 A1* | 5/2009 | Sims et al. | 600/301 |
| 2009/0156988 A1* | 6/2009 | Ferren et al. | 604/65 |
| 2009/0292222 A1* | 11/2009 | Ferren et al. | 600/549 |
| 2009/0318779 A1* | 12/2009 | Tran | 600/301 |
| 2010/0063365 A1* | 3/2010 | Pisani et al. | 600/301 |

FOREIGN PATENT DOCUMENTS

| | | | |
|---|---|---|---|
| WO | WO 9313426 A1 * | 7/1993 | |

OTHER PUBLICATIONS

Wang, Feng et al., Unconstrained cardiorespiratory monitor for premature infants, International Journal of Applied Electromagnetics and Mechanics, vol. 25, pp. 469-475, 2007, Japan.

Zuckerwar, Allan J. et al., Development of a Piezopolymer Pressure Sensor for a Portable Fetal Heart Rate Monitor, IEEE Transactions on Biomedical Engineering, vol. 40, No. 9, pp. 963-969, Sep. 1993.

* cited by examiner

600 A computer program product.

602 A signal bearing medium.

604 Machine-readable instructions, which, if executed by one or more processors, operatively enable a computing device to:

receive body motion data from a sensor unit;

detect abnormality based at least in part on analyzing data received from the sensor unit; and/or execute a series of alarm processes in response to the detected abnormality.

| 606 a computer-readable medium. | 608 a recordable medium. | 610 a communications medium. |
|---|---|---|

FIG. 6

SENSOR-BASED HEALTH MONITORING SYSTEM

BACKGROUND

In a society that may have an increasing proportion of aging individuals or that may have an increasing proportion of single person families, many individuals may be living alone. In such a society, it may be useful to establish an enhanced infrastructure for managing the health for such individuals, and for taking appropriate care of urgent cases.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

In the drawings:

FIG. 6 illustrates an example computer program product; and

DETAILED DESCRIPTION

Figure 1:
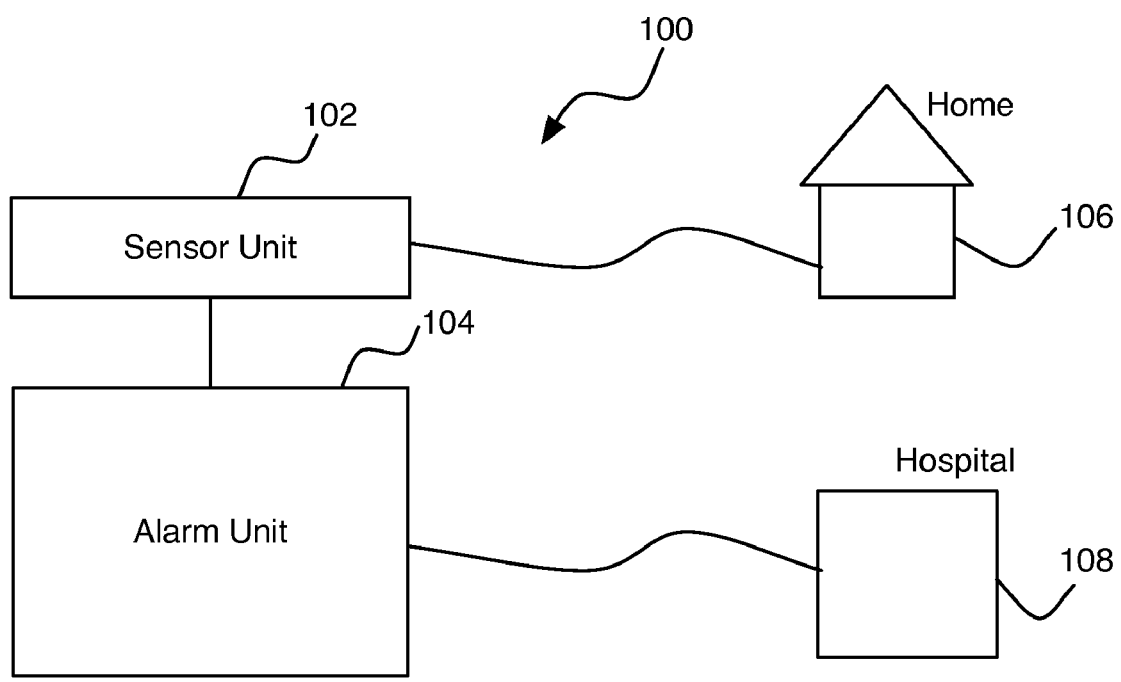
FIG. 1 illustrates a diagram of an example health monitoring system that may be arranged to monitor a user.

The following description sets forth various examples along with specific details to provide a thorough understanding of claimed subject matter. It will be understood by those skilled in the art, however, that claimed subject matter may be practiced without some or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

This disclosure is drawn, inter alia, to methods, apparatus, systems and/or computer program products related to sensor-based health monitoring systems.

The long-term continuous measurement of physiological data may be utilized to detect abnormal situations in individuals. In some instances, physiological monitoring methods may relate to the heart rate, electroencephalography (EEG), electrocardiography (ECG), body temperature, or oxygen density in blood. However, such physiological monitoring methods may not be convenient for long-term measurements. For example, ECG measurements may need electrodes to be pasted on the skin, which may reduce the suitability of ECG for long-term uses. As will be described in greater detail below, a health monitoring system may be configured to monitor body motion of a user, which may be suitable for long-term uses, for example.

FIG. 1 illustrates an example health monitoring system 100 that may be arranged to monitor a user, in accordance with at least some embodiments of the present disclosure. In the illustrated example, the health monitoring system 100 may include a sensor unit 102 that may be configured to detect body motion of a user (not shown).

The health monitoring system 100 may also include an alarm unit 104 that may be configured to analyze body motion data received from the sensor unit 102 to execute a series of alarm processing operations. For example, the alarm unit 104 may be configured to execute a series of alarm processing operations in response to the detection of body motion data from the sensor unit.

Such a health monitoring system 100, including the sensor unit 102 and the alarm unit 104, may monitor body motion of a user, detect abnormalities of such a user by analyzing body motion data, and/or execute a series of alarm processes in response to the detection of such abnormalities. Such operations will be described in greater detail below.

The alarm unit 104 may be configured to communicate with one or more remote site, such as a home 106, a hospital 108, the like, or combinations thereof. For example, the home 106 may be the home of a relative of the user.

Figure 2:
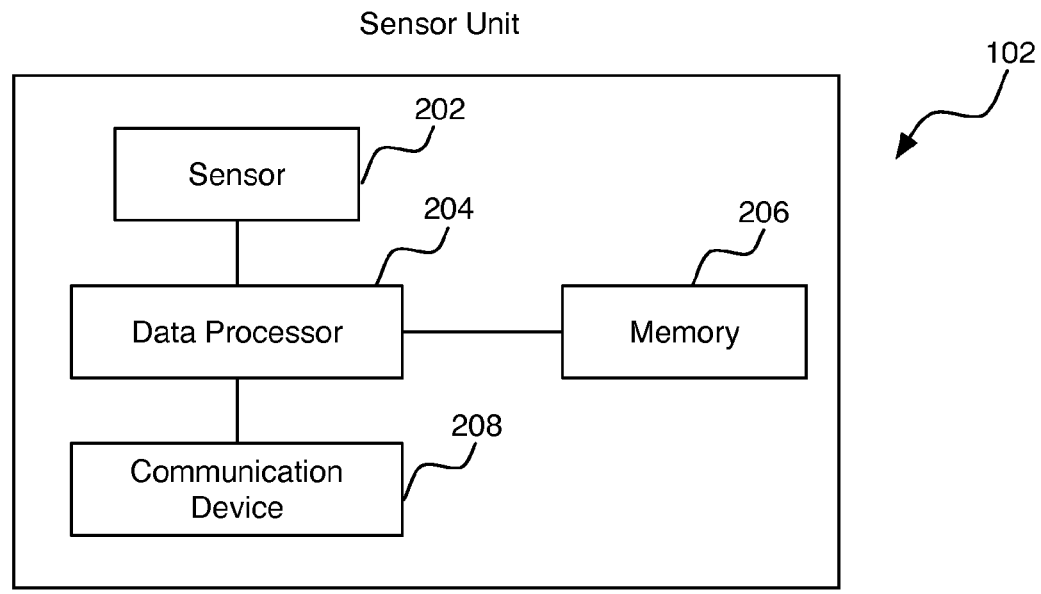
FIG. 2 illustrates a schematic diagram of an example sensor unit that may be arranged to monitor a user.

FIG. 2 illustrates a schematic diagram of an example sensor unit 102 that may be arranged to monitor a user, in accordance with at least some embodiments of the present disclosure. In the illustrated example, the sensor unit 102 may include a sensor 202. In some examples, the sensor unit 102 may be adapted to be attached to or worn by a user (not shown). For example, the sensor unit 102 may be put into a pocket of the clothing of a user, attached to a belt, or embedded in a finger ring, a bracelet, or the like for convenience of carrying such a sensor unit 102 by a user. In other examples, the sensor unit 102 may be used for a pet, animal, or the like. In such a case, the sensor unit 102 may be embedded in a collar, a bracelet, a tag, or the like.

Figure 3:
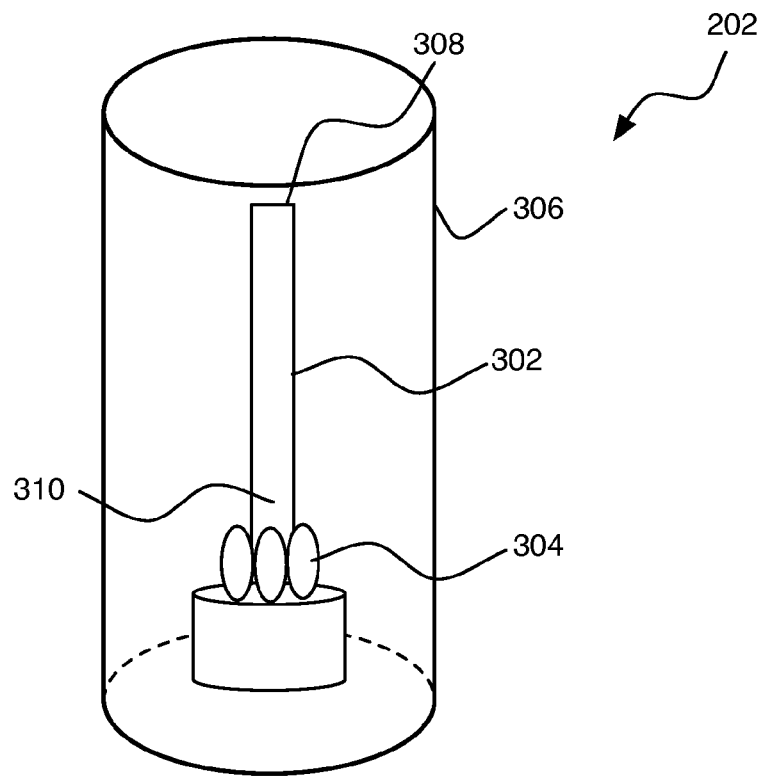
FIG. 3 illustrates a perspective diagram of an example sensor that may be arranged to monitor a user.

FIG. 3 illustrates a perspective diagram of an example sensor 202 that may be arranged to monitor a user, in accordance with at least some embodiments of the present disclosure. In the illustrated example, the sensor 202 may include an elastic member 302. The elastic member 302 may be configured to deform in response to motion of a user (not shown). In one example, the elastic member 302 may have the shape of an elongate stick. The elastic member 302 may be formed from a thin deformable metal, such as stainless steel or the like.

Additionally or alternatively, a weight (not shown) may be attached at an extremity 308 of the elastic member 302. For example, such a weight may be attached at the extremity 308 of the elastic member 302 to increase inertia, which may result in the elastic member 302 being deformed more responsive to the body motion of a user.

The sensor 202 may also include one or more elements 304 configured to detect deformation. Such elements 304 configured to detect deformation may be attached to the elastic member 302. In one example, the element 304 configured to detect deformation may include one or more piezo-elements. For example, such a piezo-element-type element 304 may be attached to a root part 310 of the elastic member 302.

Additionally or alternatively, the sensor 202 may include an acceleration-type sensor or a vibration-type sensor. Such an acceleration-type sensor or vibration-type sensor may be used in addition to or in place of the elastic member 302 and elements 304 configured to detect deformation described above.

In operation, in cases where the sensor unit 102 is moved by body motion of a user, the elastic member 302 may be bent by force of inertia. Such a bending of the elastic member 302 by force of inertia may in turn cause deformation of the elements 304 configured to detect deformation. For example, piezo-element-type element 304 configured to detect deformation may generate voltage that may be detected or measured in order to monitor such body motion of a user.

The sensor 202 may also include a housing 306 configured to house the elastic member 302, the elements 304 configured to detect deformation, and/or other elements of sensor unit 102 (FIG. 2). For example, the housing 306 may be configured to house the elastic member 302, the elements 304 configured to detect deformation, data processor 204 (FIG. 2), and communication device 208 (FIG. 2) of sensor unit 102 (FIG. 2). In one example the housing 306 may have a cylindrical type shape.

Referring back to FIG. 2, the sensor unit 102 may also include a data processor 204 operably coupled to sensor 202. The data processor 204 may be configured to measure the output of the elements 304 (FIG. 3) configured to detect deformation. In one example, the data processor 204 may be configured to process the output signals from the sensor 202, and calculate data such as frequency and/or amplitude (e.g. power) based at least in part on the output signals from the sensor 202. Such calculated data, such as frequency and/or amplitude, may be stored in memory 206.

The sensor unit 102 may also include a communication device 208 operably coupled to the data processor 204. The communication device 208 may be configured to send results measured by the data processor 204 to the alarm unit 104 (FIG. 1). In one example, the communication device 208 may include a short range communicator configured to transmit data to the alarm unit 104 (FIG. 1). For example, the communication device 208 may include a Bluetooth-type short range communicator or the like.

Figure 4:
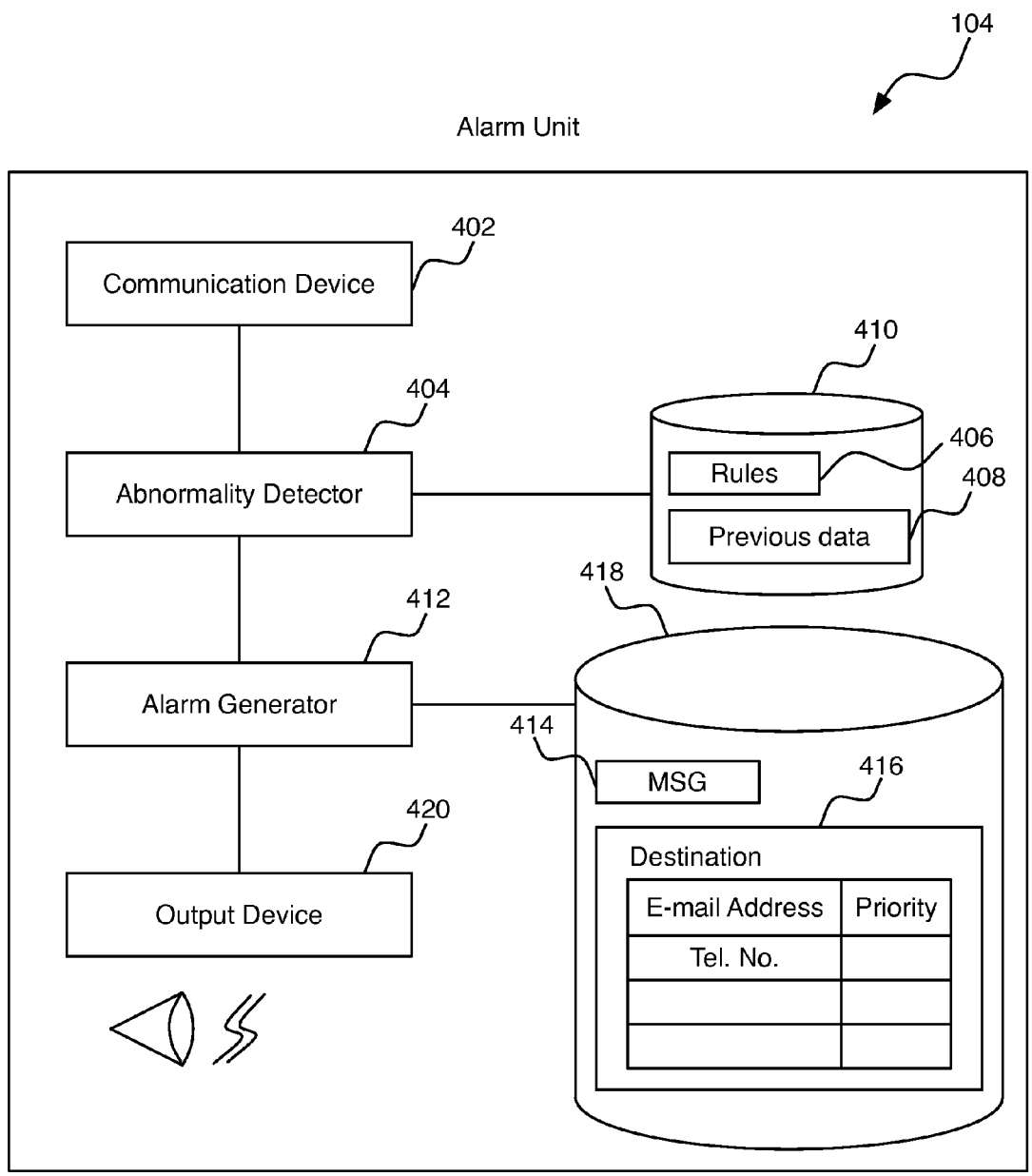
FIG. 4 illustrates a schematic diagram of an example alarm unit.

FIG. 4 illustrates a schematic diagram of an example alarm unit 104, in accordance with at least some embodiments of the present disclosure. In the illustrated example, the alarm unit 104 may include a communication device 402. The communication device 402 may be configured to receive data from the sensor unit 102 (FIG. 1). In one example, the communication device 402 may include a short range communicator configured to receive data from the sensor unit 102 (FIG. 1). For example, the communication device 402 may include a Bluetooth-type short range communicator or the like.

The alarm unit 104 may include an abnormality detector 404 operably coupled to communication device 402. The abnormality detector 404 may be configured to detect an abnormality based at least in part on an analysis of the detection of body motion data from the sensor unit 102 (FIG. 1) in accordance with at least one preprogrammed rule 406. Additionally, such an analysis of the detection of body motion data in accordance with the preprogrammed rules 406 may be based at least in part on one or more threshold values and/or previous data 408. Such rules 406, threshold values, and/or previous data 408 may be stored in a memory 410 that may be operatively associated with abnormality detector 404.

In one example, the abnormality detector 404 may be configured to change a criteria for judgment under one or more preprogrammed rules 406 based at least in part on the current clock time. For example, at night time, since the user may be in sleep, the abnormality detector 404 may be configured not to determine abnormality, even if the amplitude (e.g. power) of the body motion data from the sensor unit 102 (FIG. 1) is very low.

The abnormality detector 404 may be configured to determine such an abnormality based at least in part on a calculated frequency of the body motion data from the sensor unit 102 (FIG. 1). Additionally or alternatively, the abnormality detector 404 may be configured to determine such an abnormality based at least in part on a amplitude (e.g. power) of the body motion data from the sensor unit 102 (FIG. 1).

In one example, the abnormality detector 404 may be configured to determine such an abnormality based at least in part on an amplitude of signals from the sensor unit 102 (FIG. 1) during a predetermined period being lower than a predetermined value. For example, when the received body motion data (e.g. amplitude of signals) is relatively low (e.g. zero or near zero) for several minutes, such received body motion data may indicate that the user has not moved for several minutes. In this case, since there is a possibility of the user being down, the abnormality detector 404 may determine that an abnormality of the user has occurred.

In another example, the abnormality detector 404 may be configured to determine such an abnormality based at least in part on an amplitude of signals from the sensor unit 102 (FIG. 1) during a predetermined period being higher than a predetermined value. For example, when the received body motion data (e.g. amplitude of signals) is relatively high, especially if the received body motion data appears at a specific frequency, such received body motion data may indicate that the user is moving quickly and violently. In this case, since there is a possibility of the user being in a severe spasm, an epileptic fit, struggling to manage his/her pain, or the like, the abnormality detector 404 may determine an abnormality of the user has occurred.

Additionally or alternatively, the abnormality detector 404 may use corresponding previous data 408 as a basis for analysis. For example, the abnormality detector 404 may be configured to determine an abnormality based at least in part on a difference between an amplitude of signals from the sensor unit 102 (FIG. 1) during a predetermined period and corresponding previous data 408 being higher than a predetermined value. In this case, the abnormality detector 404 may detect that the activities of the user may be different than usual in some significant way. The alarm unit 104 may store the received body motion data as previous data 408 in the memory 410, and such previous data 408 may be associated with a time that the body motion data was received. For example, the alarm unit 104 may calculate and store an average of the body motion data for a given time of day (such as an average over a period of an hour at a specific time of day or night) as previous data 408. Accordingly, the abnormality detector 404 may be configured to determine an abnormality based at least in part on a difference between an amplitude of signals from the sensor unit 102 (FIG. 1) at a given time of day and previous data 408 corresponding to such a given time of day being higher than a predetermined value.

The alarm unit 104 may further include an alarm generator 412 operably coupled to the abnormality detector 404. The alarm generator 412 may be configured to output an alarm notification in cases where an abnormality is detected by abnormality detector 404. In one example, the alarm generator 412 may be configured to send an alarm message or an automatic call 414 to one or more predetermined sites (not shown) to notify an alarm on condition that the abnormality detector 404 has determined an abnormality. Such predetermined sites (not shown) may include remote sites, such as the home 106 (FIG. 1) (such as a home of a family member or another emergency contact person), the hospital 108 (FIG. 1), a healthcare service company, some other registered destination, the like, or combinations thereof. Destination data 416 regarding such predetermined sites (not shown) and/or the alarm message or the automatic call 414 may be stored in memory 418, which may be separate from memory 410 or integrated with memory 410. The alarm generator 412 may be configured to establish a connection with the Internet, a landline telephone network, a wireless telephone network, the like, or combinations thereof. The alarm generator 412 may be configured to make automatic calls using a computer synthesized voice.

The alarm unit 104 may include one or more output devices 420 operably coupled to the alarm unit 104. Such output devices 420 may include a speaker, a lamp, a vibrator, the like, or combinations thereof that may be configured to notify an alarm to the user or other person in the vicinity of the health monitoring system 100 (FIG. 1). Additionally, the alarm unit 104 may include a user interface (not shown) (e.g., one or more touch input devices, voice input devices, etc.) configured to permit a user or other person to acknowledge, disable, or reset such an alarm on the alarm unit 104. Such an alarm acknowledgement, disabling, or resetting may reduce or prevent the sending of an unnecessary message to a remote site. For example, the alarm generator 412 may be configured to execute a first alarm process on condition that the abnormality detector 404 determines an abnormality, and the alarm generator 412 (FIG. 4) may further be configured to execute a second alarm process on condition of receiving no response to the first alarm. In such an example, a first alarm process may be to notify the abnormality via the one or more output devices 420 connected to the alarm unit 104, and a second alarm process may be to send an alarm message to a remote site, such as a home 106 (FIG. 1), a hospital 108 (FIG. 1), the like, or a combination thereof. For example, when an abnormality is detected, the alarm generator 412 may at first notify the user of the abnormality being detected. Then, if no operation is conducted to disable such an alarm within a predetermined time period, the alarm generator 412 may send an alarm message to a remote site.

In another example, such a first alarm process may be to send an alarm message to a first place and the second alarm process may be to send an alarm message to a second place. For example, the alarm generator 412 may be configured to send an alarm message to the first place, e.g., such as a home 106 (FIG. 1) of a family member, at first. Then, if no response is received from the first place within a predetermined time period, the alarm generator 412 may send an alarm message to the second place, e.g., such as hospital 108 (FIG. 1). In this example, when there is no alarm acknowledgement, disabling, or resetting at the first place, the second place may receive an alarm message, such as medical doctor or a service company that may take care of this situation instead.

In a further example, the abnormality detector 404 may be configured to determine a level of abnormality, and the alarm generator 412 may be configured to change a manner of making an alarm consistent with such a level of abnormality. Such a level of abnormality may be set at various levels, such as low abnormality, medium abnormality, high abnormality, or the like. For example, the alarm generator 412 may be configured to change the destination to send an alarm message to, in accordance with the level of an abnormality. In such a case, if the abnormality detector 404 determines that the level of abnormality is low, the alarm generator 412 may only activate the alarm facility on the alarm unit 104 or may only send out an alarm message. In such a case, if the abnormality detector 404 determines that the level of abnormality is medium, the alarm generator 412 may be configured to make an automatic call to user's family, as the user may not be aware of the message. If the abnormality detector 404 determines that the level of abnormality is high, the alarm generator 412 may directly contact the hospital or the service company that may have an ability to take care of such high abnormality matters.

Figure 5:
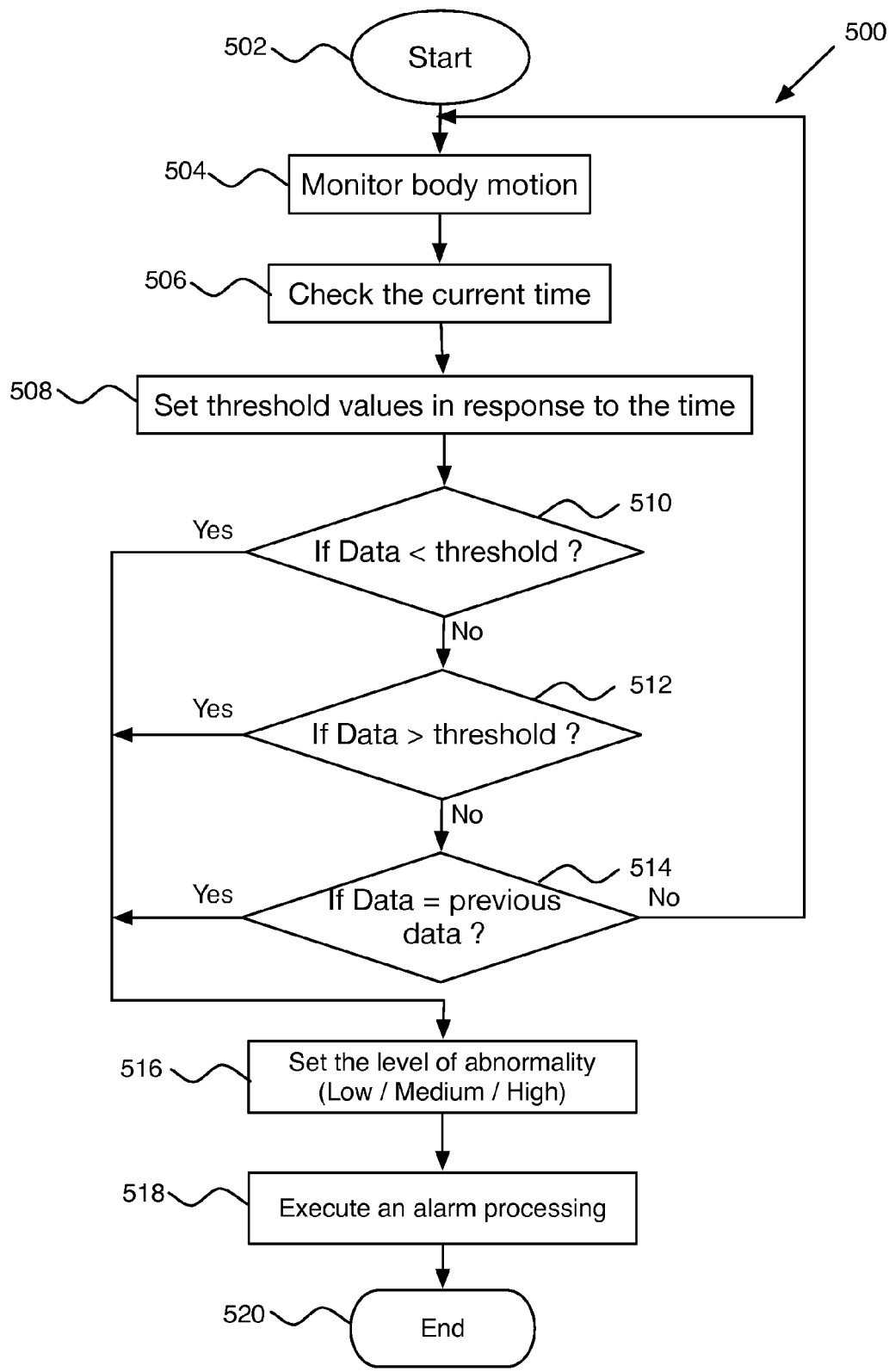
FIG. 5 illustrates an example process for sensor-based health monitoring.

FIG. 5 illustrates an example process 500 for sensor-based health monitoring, in accordance with at least some embodiments of the present disclosure. Process 500, and other processes described herein, set forth various functional blocks or actions that may be described as processing steps, functional operations, events and/or acts, etc., which may be performed by hardware, software, and/or firmware. Those skilled in the art in light of the present disclosure will recognize that numerous alternatives to the functional blocks shown in FIG. 5 may be practiced in various implementations. For example, although process 500, as shown in FIG. 5, comprises one particular order of blocks or actions, the order in which these blocks or actions are presented does not necessarily limit claimed subject matter to any particular order. Likewise, intervening actions not shown in FIG. 5 and/or additional actions not shown in FIG. 5 may be employed and/or some of the actions shown in FIG. 5 may be eliminated, without departing from the scope of claimed subject matter. Process 500 may include one or more of operations 502, 504, 506, 508, 509, 510, 512, 514, 516, 518 and/or 520.

As illustrated, process 500 may be implemented for sensor-based health monitoring of one or more users. Process 500 may begin at start block 502 and proceed to operation 504. At operation 504, body motion of a user (not shown) may be detected or monitored. For example, the body motion of a user may be detected or monitored via sensor unit 102 (FIG. 1) of health monitoring system 100 (FIG. 1).

As will be described in greater detail below with respect to operations 506-518 preprogrammed rules may be implemented by an analysis of data regarding body motion to detect abnormalities. For example, data regarding body motion received from the sensor unit 102 (FIG. 1) of health monitoring system 100 (FIG. 1) may be analyzed via alarm unit 104 (FIG. 1) of health monitoring system 100 (FIG. 1) according to preprogrammed rules.

At operation 506, a current clock time may be checked. For example, the current clock time may be checked via alarm unit 104 (FIG. 1) of health monitoring system 100 (FIG. 1).

At operation 508, one or more threshold values may be set in response to the current clock time. For example, such threshold values may be set via alarm unit 104 (FIG. 1) of health monitoring system 100 (FIG. 1). In one example, the abnormality detector 404 (FIG. 4) of alarm unit 104 (FIG. 4) may set the one or more threshold values in response to the current clock time. For example, the abnormality detector 404 (FIG. 4) may be configured to change a criteria for judgment under one or more preprogrammed rules based at least in part on the current clock time.

At operation 510, process 500 may determine whether the data regarding body motion is less than the one or more threshold values. Process 500 continues from decision operation 510 to operation 516 the data regarding body motion is less than the one or more threshold values. Otherwise, process 500 may continue from decision operation 510 to operation 512 when the data regarding body motion is not less than the one or more threshold values. For example, such a determination of whether the data regarding body motion is less than the one or more threshold values may be determined via alarm unit 104 (FIG. 1) of health monitoring system 100 (FIG. 1). In one example, the abnormality detector 404 (FIG. 4) of alarm unit 104 (FIG. 4) may determine whether the data regarding body motion is less than the one or more threshold values. For example, the abnormality detector 404 (FIG. 4) may be configured to determine an abnormality based at least in part on an amplitude of signals from the sensor unit 102 (FIG. 1) during a predetermined period being lower than a predetermined threshold value.

At operation 512, process 500 may determine whether the data regarding body motion is greater than the one or more threshold values. The threshold values at operation 512 are generally greater than the threshold values at operation 510. Process 500 continues from decision operation 512 to operation 516 when the data regarding body motion is greater than the one or more threshold values. Otherwise, process 500 may continue from decision operation 512 to operation 514 when the data regarding body motion is not greater than the one or more threshold values. For example, such a determination of whether the data regarding body motion is greater than the one or more threshold values may be determined via alarm unit 104 (FIG. 1) of health monitoring system 100 (FIG. 1). In one example, the abnormality detector 404 (FIG. 4) of alarm unit 104 (FIG. 4) may determine whether the data regarding body motion is greater than the one or more threshold values. For example, the abnormality detector 404 (FIG. 4) may be configured to determine an abnormality based at least in part on an amplitude of signals from the sensor unit 102 (FIG. 1) during a predetermined period being higher than a predetermined threshold value.

At operation 514, process 500 may determine whether the data regarding body motion is not equal or not approximately equal to previous data regarding body motion. Process 500 continues from decision operation 514 to operation 516 when the data regarding body motion is not equal or not approximately equal to previous data regarding body motion. Otherwise, process 500 may continue from decision operation 514 to operation 504 when the data regarding body motion is equal or approximately equal to previous data regarding body motion. For example, such a determination of whether the data regarding body motion is not equal or not approximately equal to previous data regarding body motion may be determined via alarm unit 104 (FIG. 1) of health monitoring system 100 (FIG. 1). In one example, the abnormality detector 404 (FIG. 4) of alarm unit 104 (FIG. 4) may determine whether the data regarding body motion is not equal or not approximately equal to previous data regarding body motion. For example, the abnormality detector 404 (FIG. 4) may be configured to determine an abnormality based at least in part on a difference between an amplitude of signals from the sensor unit 102 (FIG. 1) during a predetermined period and corresponding data in the past being higher than a predetermined value.

Operations 510, 512, and 514 may be utilized singly or in various combinations with one another to determine one or more abnormalities. For example, only operation 510, only operation 512, or only operation 514 may be utilized to determine an abnormality. Alternatively, operation 510, operation 512, and operation 514 may be utilized in various combinations with one another to determine one or more abnormalities.

At operation 516, a level of abnormality may be set. For example the level of abnormality may be set at various levels, such as low abnormality, medium abnormality, or high abnormality, via alarm unit 104 (FIG. 1) of health monitoring system 100 (FIG. 1). In one example, the abnormality detector 404 (FIG. 4) of alarm unit 104 (FIG. 4) may be configured to determine a level of abnormality. Additionally, the alarm generator 412 (FIG. 4) may be configured to change a manner of making an alarm based at least in part on the determined level of abnormality.

At operation 518, in cases where an abnormality is determined, a series of one or more alarm process operations may be conducted in response to the determined abnormality. For example the series of one or more alarm process operations may be conducted via alarm unit 104 (FIG. 1) of health monitoring system 100 (FIG. 1). In one example, the alarm generator 412 (FIG. 4) of alarm unit 104 (FIG. 1) may be configured to send or call to one or more predetermined sites to notify an alarm on condition that the abnormality detector 404 (FIG. 4) determines an abnormality. Process 500 may then proceed to end block 520.

In one example, the alarm generator 412 (FIG. 4) may be configured to execute a first alarm process on condition that the abnormality detector 404 (FIG. 4) determines an abnormality, and the alarm generator 412 (FIG. 4) may further be configured to execute a second alarm process on condition of receiving no response to the first alarm. For example, such a first alarm process may be to notify the abnormality via one or more output devices 420 (FIG. 4) connected to the alarm unit alarm unit 104 (FIG. 1), and such a second alarm process may be to send an alarm message to a remote site, such as a home 106 (FIG. 1), a hospital 108 (FIG. 1), the like, or a combination thereof. Additionally or alternatively, such a first alarm process may be to send an alarm message to a first place, e.g., such as a home 106 (FIG. 1), and the second alarm process may be to send an alarm message to a second place, e.g., such as hospital 108 (FIG. 1).

In operation, in operation process 500 may operate so that an alarm message or call may be sent to a registered destination via the alarm unit 104 (FIG. 1).

In a further example, process 500 may operate so that a beep-type alarm, a light-type alarm, a vibration-type alarm, the like, or combinations thereof may be activated via the alarm unit 104 (FIG. 1). If such an alarm is not disabled, an alarm message or call may be sent to a registered destination via the alarm unit 104 (FIG. 1).

In a still further example, process 500 may operate so that a call may be placed to a family member or the like via the alarm unit 104 (FIG. 1). If no response is received from such a call, an alarm message or call may be sent to a hospital 108 (FIG. 1) or the like via the alarm unit 104 (FIG. 1).

In another example, process 500 may operate so that a level of abnormality may be checked. In cases where the level of abnormality is low a beep-type alarm, a light-type alarm, a vibration-type alarm, the like, or combinations thereof may be activated via the alarm unit 104 (FIG. 1), for example. In cases where the level of abnormality is medium a call may be placed to a family member or the like via the alarm unit 104 (FIG. 1). In cases where the level of abnormality is high a call may be placed to a hospital 108 (FIG. 1) or the like via the alarm unit 104 (FIG. 1).

FIG. 6 illustrates an example computer program product 600 that is arranged in accordance with the present disclosure.

Program product 600 may include a signal bearing medium 602. Signal bearing medium 602 may include one or more machine-readable instructions 604, which, if executed by one or more processors, may operatively enable a computing device to provide the functionality described above with respect to FIG. 5. Thus, for example, referring to the system of FIG. 1, health monitoring system 100, sensor unit 102, and/or alarm unit 104 may undertake one or more of the actions shown in FIG. 5 in response to instructions 604 conveyed by medium 602.

In some implementations, signal bearing medium 602 may encompass a computer-readable medium 606, such as, but not limited to, a hard disk drive, a Compact Disc (CD), a Digital Versatile Disk (DVD), a digital tape, memory, etc. In some implementations, signal bearing medium 602 may encompass a recordable medium 608, such as, but not limited to, memory, read/write (R/W) CDs, R/W DVDs, etc. In some implementations, signal bearing medium 602 may encompass a communications medium 610, such as, but not limited to, a digital and/or an analog communication medium (e.g., a fiber optic cable, a waveguide, a wired communications link, a wireless communication link, etc.).

Figure 7:
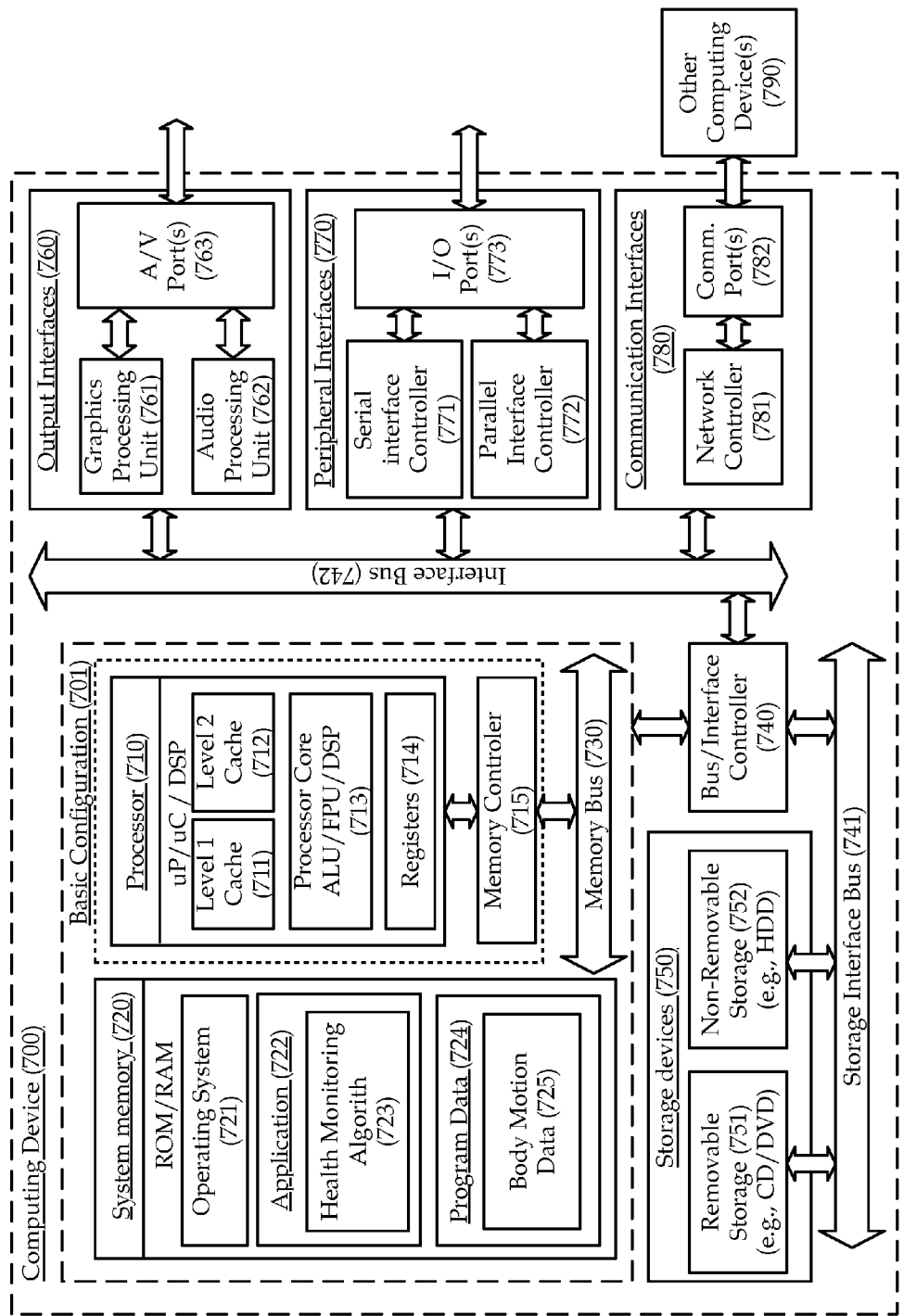
FIG. 7 is a block diagram illustrating an example computing device, all arranged in accordance with the present disclosure.
Figure 7:
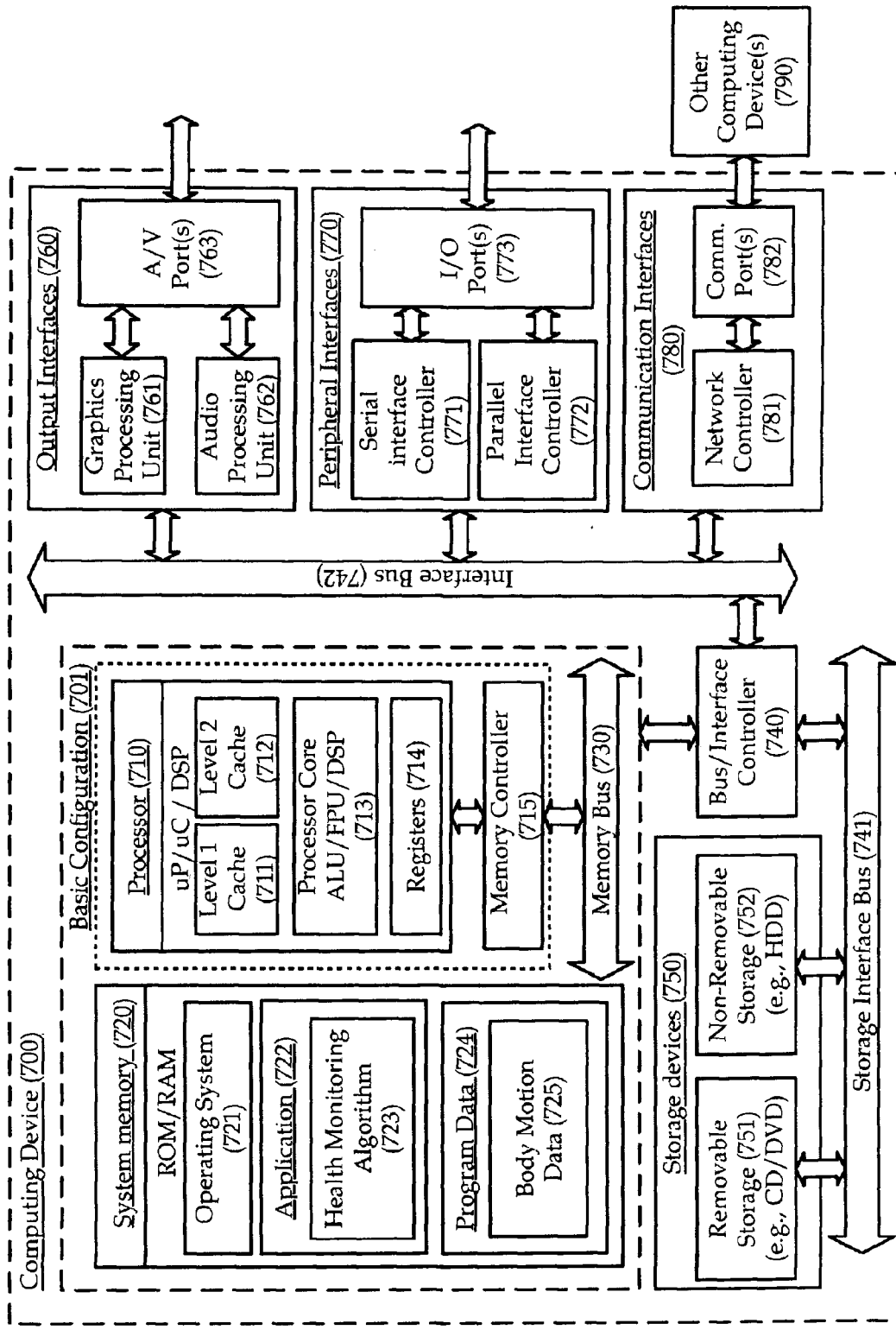

FIG. 7 is a block diagram illustrating an example computing device 700 that is arranged in accordance with the present disclosure. In one example configuration 701, computing device 700 may include one or more processors 710 and system memory 720. A memory bus 730 can be used for communicating between the processor 710 and the system memory 720.

Depending on the desired configuration, processor 710 may be of any type including but not limited to a microprocessor (µP), a microcontroller (µC), a digital signal processor (DSP), or any combination thereof. Processor 710 can include one or more levels of caching, such as a level one cache 711 and a level two cache 712, a processor core 713, and registers 714. The processor core 713 can include an arithmetic logic unit (ALU), a floating point unit (FPU), a digital signal processing core (DSP Core), or any combination thereof. A memory controller 715 can also be used with the processor 710, or in some implementations the memory controller 715 can be an internal part of the processor 710.

Depending on the desired configuration, the system memory 720 may be of any type including but not limited to volatile memory (such as RAM), non-volatile memory (such as ROM, flash memory, etc.) or any combination thereof. System memory 720 may include an operating system 721, one or more applications 722, and program data 724. Application 722 may include a health monitoring algorithm 723 in a health monitoring system 100, sensor unit 102, and/or alarm unit 104 (FIG. 1) that is arranged to perform the functions and/or operations as described herein including the functional blocks and/or operations described with respect to process 500 of FIG. 5. Program Data 724 may include body motion data 725 for use in health monitoring algorithm 723. In some example embodiments, application 722 may be arranged to operate with program data 724 on an operating system 721 such that implementations of mobile sampling may be provided as described herein. This described basic configuration is illustrated in FIG. 7 by those components within dashed line 701.

Computing device 700 may have additional features or functionality, and additional interfaces to facilitate communications between the basic configuration 701 and any required devices and interfaces. For example, a bus/interface controller 740 may be used to facilitate communications between the basic configuration 701 and one or more data storage devices 750 via a storage interface bus 741. The data storage devices 750 may be removable storage devices 751, non-removable storage devices 752, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 720, removable storage 751 and non-removable storage 752 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 700. Any such computer storage media may be part of device 700.

Computing device 700 may also include an interface bus 742 for facilitating communication from various interface devices (e.g., output interfaces, peripheral interfaces, and communication interfaces) to the basic configuration 701 via the bus/interface controller 740. Example output interfaces 760 may include a graphics processing unit 761 and an audio processing unit 762, which may be configured to communicate to various external devices such as a display or speakers via one or more A/V ports 763. Example peripheral interfaces 760 may include a serial interface controller 771 or a parallel interface controller 772, which may be configured to communicate with external devices such as input devices (e.g., keyboard, mouse, pen, voice input device, touch input device, etc.) or other peripheral devices (e.g., printer, scanner, etc.) via one or more I/O ports 773. An example communication interface 780 includes a network controller 781, which may be arranged to facilitate communications with one or more other computing devices 790 over a network communication via one or more communication ports 782. A communication connection is one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), infrared (IR) and other wireless media. The term computer readable media as used herein may include both storage media and communication media.

Computing device 700 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. Computing device 700 may also be implemented as a personal computer including both laptop computer and non-laptop computer configurations. In addition, computing device 700 may be implemented as part of a wireless base station or other wireless system or device.

Some portions of the foregoing detailed description are presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm is here, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing device, that manipulates or transforms data represented as physical electronic or magnetic quantities within memories, registers, or other information storage devices, transmission devices, or display devices of the computing device.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In some embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a flexible disk, a hard disk drive (HDD), a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While certain exemplary techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter also may include all implementations falling within the scope of the appended claims, and equivalents thereof.

What is claimed is:

1. A health monitoring system, comprising:
   a sensor unit configured to detect body motion and adapted to be attached to or worn by a user, including:
      an elastic member substantially shaped as an elongate stick; and
      an element attached to the elastic member configured to detect deformation and generate an output signal in response to the detected deformation; and
   an alarm unit configured to receive the output signal and execute a series of alarm processing operations in response to the output signal.

2. A health monitoring system as recited in claim 1, wherein the sensor unit further comprises:
   a data processor configured to measure the output signal to provide a processed result; and
   a communication device configured to send the processed result.

3. A health monitoring system as recited in claim 1, wherein the alarm unit further comprises:
   a communication device configured to receive the output signal;
   an abnormality detector configured to detect an abnormality based at least in part on an analysis of the output signal in accordance with at least one preprogrammed rule; and
   an alarm generator configured to output an alarm notification.

4. A health monitoring system as recited in claim 3, wherein the abnormality detector is configured to determine the abnormality based at least in part on an amplitude of signals from the output signal during a predetermined period being lower than a predetermined value.

5. A health monitoring system as recited in claim 3, wherein the abnormality detector is configured to determine the abnormality based at least in part on an amplitude of signals from the output signal during a predetermined period being higher than a predetermined value.

6. A health monitoring system as recited in claim 3, wherein the abnormality detector is configured to determine the abnormality based at least in part on a difference between an amplitude of signals from the output signal during a predetermined period and corresponding data in the past being higher than a predetermined value.

7. A health monitoring system as recited in claim 4, wherein the abnormality detector is configured to change a criteria for judgment under the at least one preprogrammed rule based at least in part on a current clock time.

8. A health monitoring system as recited in claim 5, wherein the abnormality detector is configured to change a criteria for judgment under the at least one preprogrammed rule based at least in part on a current clock time.

9. A health monitoring system as recited in claim 3, wherein the alarm generator is configured to send or call to one or more predetermined sites to notify an alarm on condition that the abnormality detector determines abnormality.

10. A health monitoring system as recited in claim 3, wherein the alarm generator is configured to execute a first alarm process on condition that the abnormality detector determines abnormality, and the alarm generator further is configured to execute a second alarm process on condition of receiving no response to the first alarm.

11. A health monitoring system as recited in claim 10, wherein the first alarm process is to notify the abnormality via one or more output devices connected to the alarm unit, and the second alarm process is to send an alarm message to a remote site.

12. A health monitoring system as recited in claim 10, wherein the first alarm process is to send an alarm message to a first place, and the second alarm process is to send an alarm message to a second place.

13. A health monitoring system as recited in claim 3, wherein the abnormality detector is configured to determine a level of abnormality, and the alarm generator is configured to change a manner of making an alarm.

14. A health monitoring method, comprising:
   detecting body motion by using a sensor unit adapted to be attached to or worn by a user, including:
      an elastic member substantially shaped as an elongate stick; and
      an element attached to the elastic member configured to detect deformation and generate an output signal in response to the detected deformation;
   detecting an abnormality based at least in part on analyzing the output signal; and
   executing a series of alarm processes in response to the detected abnormality.

15. An article comprising:
   a signal bearing medium comprising machine-readable instructions stored thereon, which, if executed by one or more processors, operatively enable a computing device to:
   receive body motion data from a sensor unit adapted to be attached to or worn by a user, including:
      an elastic member substantially shaped as an elongate stick; and
      an element attached to the elastic member configured to detect deformation and generate an output signal in response to the detected deformation;
   detect an abnormality based at least in part on analyzing the output signal; and
   execute a series of alarm processes in response to the detected abnormality.

* * * * *

UNITED STATES PATENT AND TRADEMARK OFFICE
CERTIFICATE OF CORRECTION

PATENT NO. : 8,172,777 B2
APPLICATION NO. : 12/559228
DATED : May 8, 2012
INVENTOR(S) : Goto It is certified that error appears in the above-identified patent and that said Letters Patent is hereby corrected as shown below:

In the Drawings:

In Fig. 7, Sheet 6 of 6, in Box "(723)", in Line 2, delete "Algorith" and insert -- Algorithm --, therefor.

In Fig. 7, Sheet 6 or 6, in Box "(715)", in Line 1, delete "Controler" and insert -- Controller --, therefor.

In the drawings, Fig. 7 should be replaced with the corrected Fig. 7 as shown on the attached page.

In the Specifications:

In Column 6, Line 39, delete "509,".

In Column 10, Line 5, delete "(HDD)," and insert -- (HDDs), --, therefor.

In Column 10, Line 7, delete "(SSD)," and insert -- (SSDs), --, therefor.

Signed and Sealed this
Thirteenth Day of August, 2013

Teresa Stanek Rea
*Acting Director of the United States Patent and Trademark Office*